United States Patent [19]
Amagaya et al.

[11] Patent Number: 5,393,740
[45] Date of Patent: Feb. 28, 1995

[54] NEUROTENSIN HEXAPEPTIDES

[75] Inventors: Sakae Amagaya, Ami; Tadami Fujiwara, Tokyo; Masaki Aburada, Tokyo; Michio Nagasawa, Tokyo; Tsutomu Oyama, Ami, all of Japan

[73] Assignee: Tsumura & Co., Tokyo, Japan

[21] Appl. No.: 920,878

[22] Filed: Jul. 28, 1992

[30] Foreign Application Priority Data

Jul. 30, 1991 [JP] Japan .................. 3-211416

[51] Int. Cl.$^6$ .............. A61K 37/00; A61K 37/02; C07K 5/00; C07K 7/00
[52] U.S. Cl. .......................... 514/17; 514/16; 530/329; 530/328; 530/330
[58] Field of Search ............ 530/330, 329, 328; 514/17, 16

[56] References Cited

U.S. PATENT DOCUMENTS

| | | | |
|---|---|---|---|
| 4,411,890 | 10/1983 | Momany | 424/177 |
| 4,425,269 | 1/1984 | Christy et al. | 530/330 |
| 4,732,890 | 3/1988 | Bonelli et al. | 514/11 |

FOREIGN PATENT DOCUMENTS 0333071 9/1989 European Pat. Off. .
1-316399 12/1989 Japan .

OTHER PUBLICATIONS

C. Granier et al, "Synthesis and Characterization of Neurotensin Analogues for Structure/Activity Relationship Studies", Eur. J. Biochem., vol. 124, 1982, pp. 117–125.

Yajima et al., Chem. Pharm. Bull., vol. 29 No. 9, pp. 2587–2591, 1981.
Sagi–Eisenburg et al., Chem Abstr., vol. 98, No. 17, p. 76, Abst No (98: 137759x).

Primary Examiner—Robert J. Hill, Jr.
Assistant Examiner—A. M. Davenport
Attorney, Agent, or Firm—Nixon & Vanderhye

[57] ABSTRACT

A hexapeptide represented by formula (II):

$$A\text{-}B\text{-}Pro\text{-}C\text{-}D\text{-}E \qquad (I)$$

where A represents an L- or D- form of arginine or lysine whose N-terminal amino group is alkylated or acylated, B represents an L- or D- form of argine, lysine, or histidine, Pro represents an L- or D- form of proline, C represents an L- or D- form of tyrosine, tryptophan, or phenylalanine, D represents an L- or D-form of valine, isolencine, or leucine, and E represents an L-or D- form of valine, isolencine, or lencine, one of the hydrogen atoms of the amino group of which may be substituted a $C_1$ to $C_4$ alkyl group, and C-terminal carboxyl group of which is substituted with —COOR*, —CH$_2$OR, or —CONHR wherein R* represents a $C_1$ to $C_4$ alkyl group, and R represents a hydrogen atom or an $C_1$ to $C_4$ alkyl group. The hexapeptide or a pharmaceutically acceptable salt of the hexapeptide is useful as medical agent such as an anti-edematous agent, an anti-shock agent, an anti-thrombus agent, an anti-arteriosclerotic agent, an anti-allergic agent, a hypotensive agent, a wound healing agent, and an anti-inflammatory agent.

6 Claims, No Drawings

NEUROTENSIN HEXAPEPTIDES

BACKGROUND OF THE INVENTION

1. Field of the Invention

The present invention relates to a novel hexapeptide and a pharmaceutically acceptable salt thereof. The hexapeptide has an increasing vascular permeability suppression action, an anti-edematous action, an anti-inflammatory action, an vascular endothelial disorder amelioration action, a hypotensive action, an protease inhibition action an anti-desseminated intravasscular coagulation syndrome (DIC) action, and a wound healing action. The hexapeptide can be useful as a medical product such as an anti-edematous agent, an anti-shock agent, an anti-thrombus agent, an anti-arteriosclerotic agent, an anti-allergic agent, a hypotensive agent, a wound healing agent, and an anti-inflammatory agent.

2. Description of the Related Art

In a conventional therapy for edematous such as a cerebral edema, a therapeutical method is most widely applied which uses an osmotic diuretic agent to elevate a hydrostatic pressure of a blood and introduce a water in the blood. In this method, a hypertonic solution of a diuretic agent such as glycerol or mannitol is quickly injected intravenously three or four times a day. Each injection time takes about 30 minutes to an hour.

This method, however, requires complicated administration control. The does of the osmotics diuretic agent must be changed according to the pathology and condition of the patients. Further, administration of the osmotic diuretic agent mentioned above must be carefully controlled since the agent causes side effects such as disturbance of an electrolyte and dehydration.

Antibiotics are mainly used in conventional therapy for septicemia. But, since the antibiotics cannot suppress the increasing vascular increasing permeability, shocks cannot be often remedied satisfactorily in the therapy using the antibiotics. Adrenal cortical hormones are also used together with the above antibiotics for suppressing the increasing vascular permeability. However, a large dose of steroids such as adrenal cortical hormones causes side effects such as an immuno-suppression, an electrolytic abnormality, and a rebound phenomenon.

As described above, a medicament has not yet been found which can suppress the increasing vascular permeability in the edematous and the septicemia, can cause little side effects, and not require the complicated administration for dosage.

SUMMARY OF THE INVENTION

Accordingly, an object of the present invention is to provide a novel compound which has an increasing vascular permeability suppression action, and causes little side effects, when administered.

Another object of the invention is to provide a pharmanceutical agent which does not require complicated administration control.

The present invention provides a hexapeptide represented by formula (I):

$$A\text{-}B\text{-}Pro\text{-}C\text{-}D\text{-}E \qquad (I)$$

where A represents an L- or D- form of arginie or lysine whose N-terminal amino group is deaminated, B represents an L- or D- form of arginine, lysine or histidine, Pro represents an L- or D- form of proline, C represents an L- or D- form of tyrosine, tryptophan, or phenylalanine, D represents an L- or D- form of valine, isoleucine, or lencine, and E represents an L- or D- form of valine, isoleucine, or lincine, one of the hydrogen atoms of the amino group of which may be substituted with a $C_1$ to $C_4$ alkyl group, and C-terminal carboxyl group of which may be substituted with $-COOR^*$, $-CH_2OR$ or $-CONHR$ wherein $R^*$ represents a $C_1$ to $C_4$ alkyl group, and R represents a hydrogen atom or a $C_1$ to $C_4$ alkyl group; or a pharmaceutically acceptable salt of the hexapeptide.

The present invention also provides a hexapeptide represented by formula (II):

$$A\text{-}B\text{-}Pro\text{-}C\text{-}D\text{-}E \qquad (II)$$

where A represents an L- or D- form of arginie or lysine whose N-terminal amino group is deaminated, B represents an L- or D- form of arginine, lysine or histidine, Pro represents an L- or D- form of proline, C represents an L- or D- form of tyrosine, tryptophan, or phenylalanine, D represents an L- or D- from of valine, isoleucine, or lencine, and E represents a L- or D- form of valine, isoleucine, or lincine, one of the hydrogen atoms of the amino group of which may be substituted with a $C_1$ to $C_4$ alkyl group, and C-terminal carboxyl group of which is substituted with $-COOR^*$, $-CH_2OR$ or $-CONHR$ wherein $R^*$ represents a $C_1$ to $C_4$ alkyl-group, and R represents a hydrogen atom or a $C_1$ to $C_4$ alkyl group; or a pharmaceutically acceptable salt of the hexapeptide.

The hexapeptide or its salt of the invention has, in addition to a vascular permeability acceleration suppression action noted above, an anti-edematous action, an anti-inflammatory action, a vascular endothelial disorder amelioration action, a hypotensive action, a protease inhibition action, anti-DiC action, and a wound healing action. Thus, the hexapeptide or its salt of the invention may be useful as an active ingredient for a pharmaceutial agent such as an anti-edematous agent, an anti-shock agent, an anti-thrombus agent, an anti-arteriousclerotic agent, an anti-allergic agent, a hypotensive agent, a wound healing agent, or an anti-inflammatory agent.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

DETAILED DESCRIPTION OF THE PREFERRED EMBODIMENTS

The present inventions are described in detail below.

The hexapeptide represented by formulas (I) and (II), and pharmaceutically acceptable salts thereof are sometimes referred to as hexapeptide compound of the present invention below.

Amino acids used in this specification are also abbreviated according to a method employed in an IUPAC-IUB Committee of Biochemical Nomenclature (CBN) and are exemplified as follows:

| | |
|---|---|
| Arg: | L-arginine |
| Ile: | L-isoleucine |
| Lys: | L-lysine |

-continued

| | |
|---|---|
| Pro: | L-proline |
| Trp: | L-tryptophan |
| D-Arg: | D-arginine |
| D-Ile: | D-isoleucine |
| D-Lys: | D-lysine |
| D-Pro: | D-proline |
| D-Trp: | D-tryptophan |
| His: | L-histidine |
| Leu: | L-leucine |
| Phe: | L-phenylalanine |
| Tyr: | L-tyrosine |
| Val: | L-valine |
| D-His: | D-histidine |
| D-Leu: | D-leucine |
| D-Phe: | D-phenylalanine |
| D-Tyr: | C-tyrosine |
| D-Val: | L-valine |

The six amino acids which constitute the hexapeptide of the present invention may either be of L-type or D-type.

In the formulas (I) and (II), the first amino acid from N terminal of the hexapeptide, represented by A, is an arginine or lysine whose N-terminal amino group is deaminated (Formula (I)), or alkylated or acylated (Formula (II)).

As regard to the deamination of the N-terminal amino group of the amino acid A, when the deaminated arginine is prepared, for example, 5-aminovaleric acid is disolvented in a 2N-sodiume hydroxide solution, then S-methylthiocarbamide is added to the solution, thereby obtaining the deaminated arginine.

The alkyl group which is introduced to the N-terminal amino group of the amino acid A may be, e.g., methyl, ethyl, propyl and butyl. The alkylation of the N-terminal amino group may be carried out, for example, by reacting the amino acid A with a corresponding alkyl iodide such as methyl iodide or ethyl iodide in an organic solvent such as acetone.

The acyl group which is introduced to the N-terminal amino group of the amino acid A may be, e.g., formyl, acethyl, propionyl, benzoyl or p-tolune sulfonyl. The acylation of the N-terminal amino group may be carried out, for example, by reacting the amino acid A with an acid anhydride such as acetic anhydride or an acid chloride such as acetyl chloride in an organic solvent such as methyl chloride or pyridine.

In the formulas (I) and (II), the peptide bond between the fifth amino acid (represented by D) and the sixth amino acid (represented by E) from N-terminal of the hexapeptide is represented by formula (III):

(III)

where X represents a hydrogen atom or $C_1$ to $C_4$ alkyl group.

In the formula (III), the alkyl group may be metyl, ethyl, n-propyl, t-propyl, n-butyl, i-butyl or t-butyl.

In the formulas (I) and (II), the sixth amino acid from N terminal of the hexapeptide, represented by E, is a valine, isoleusine or leusine. When the first amino acid A is deaminated, the C-terminal carboxyl group of the sixth amino acid E may, or may not be, substituted with —COOR*, —CH$_2$OR or —CONHR where R* represents $C_1$ to $C_4$ alkyl group, and R represents a hydrogen atom or a $C_1$ to $C_4$ alkyl group (Formula (I)). The alkyl group may be, e.g., methyl, ethyl, n-propyl, t-propyl, n-butyl, i-butyl and t-butyl. When the first amino acid A is alkylated or acylated, the C-terminal carboxyl group of the sixth amino acid E is substituted with —COOR*, —CH$_2$OR or —CONHR mentioned above (Formula (II)).

An introduction of the substitution group to the C-terminal carboxyl group for example can be achieved by, for example, the alkylation as described above.

The hexapeptides according to the present invention can be synthesized by a liquid- or solid-phase method which is a known method in peptide synthesis. A peptide synthesis using the solid-phase method will be described in detail below.

In the solid-phase method, the six amino acids are sequentially condensed, using an organic solvent-insoluble resin, starting from the amino acid of the C-terminal of the hexapeptide and is then treated with an acid, thereby obtaining the hexapeptide in a free form.

The organic solvent-insoluble resin is preferred to be chemically stable in an organic solvent and have good swell characteristic. The organic solvent-insoluble resin is exemplified by a resin obtained by introducing a side functional group such as a chloromethyl group or a hydroxymethyl group into a styrene-divinylbenzene copolymer. The functional group is activated prior to the synthesis of the hexapeptide. The carboxy group of the amino acid E is coupled to the activated functional group of the resin.

In the solid-phase synthesis, only an α-amino group or both the α-amino group and a side-chain functional group of the amino acids which constitute the hexapeptide of the present invention is protected by a protective group, and the protected amino acids are used in the synthesis of the hexapeptide. Examples of the protective group of the α-amino group are a t-butyloxycarbonyl group (Boc), a 9-fluorenylmethyloxycarbonyl group (Fmoc), or their equivalent groups. Examples of a protective group for a phenolic hydroxyl group of tyrosine are a benzyl group (Bzl), a 2,6-dichlorobenzyl group (Cl$_2$-Bzl) as a derivative thereof, an o-bromobenzyloxycarbonyl group (Br-Z), and their equivalent groups. Leucine and isoleucine can be generally used as protected by the Boc or Fmoc. These protected amino acids can be commercially available products.

The synthesis of the hexapeptide according to the present invention will be described in more detail below.

(1) Introduction of Constituent Amino Acid

Prior to peptide synthesis, an organic solvent-insoluble resin (resin) as mentioned above must be activated. This activation can be performed as follows.

The resin is placed in a peptide solid-phase method reaction vessel, methylene chloride is added thereto. Then, and a 10% triethylamine (TEA)/methylene chloride mixed solution is added thereto a total of once to three times. Every time the 10% TEA/methylene chloride is added, the resultant mixture is stirred for 5 to 10 minutes. The mixture is then filtered and the resin is washed. In this activated resin, TEA (amino group) is attached to the functional group of the resin.

The reaction vessel as described above may have a charge port for charging a reagent including the protected amino acids, a solvent, and the like and a filter for filtering the solvent, and may allow a reaction of the resin and the reagent by shaking of the vessel or stirring of the contents. The reaction vessel is preferably made of glass or Teflon (Trade mark) and allows filtering by raising or reducing a pressure in the reaction vessel.

About 2 to 20 ml of a solvent, such as methylene chloride, chloroform, dimethylformamide (DMF), or benzene, which can swell the resin are added to 1 g of the resin activated as described above to obtain a suspension. About 1 to 6 equivalent weight of a C-terminal amino acid whose α-amino group is protected by the protective group with respect to one equivalent weight of the activated functional group of the resin is added in the obtained suspension. The C-terminal amino acid is corresponding to the sixth amino acid from N-terminal of the hexapeptide of the present invention and is represented by E in the formulas (I) and (II). The resultant mixture is stirred or shaken for about 1 to 20 minutes.

About 0.5 to 2 equivalent weight of a coupler which couples the C-terminal amino acid with the functional group of the resin is added to the suspension per equivalent weight of the C-terminal amino acid, and the suspension is stirred or shaken, thereby coupling C-terminal carboxyl group of the C-terminal amino acid to the activated resin.

Examples of the coupler are dicyclohexylcarbodiimide (DCC), water-soluble carbodiimide, carbonyldiimidazole, a Woodword's reagent "K", N-ethyl-2-hydroxybenzisoxazolium trifluoroborate, 1-ethoxycarbonyl-2-ethoxy-1-2-dihydroxyquinoline, a "Bop reagent", and diphenylphosphorylazido.

The degree of progress of the coupling reaction can be monitored by a ninhydrin reagent or a fluorescamine test. When the reaction is not completed, coupling is repeated.

Alternatively, the amino acid whose α-amino group is protected can also be combined to a resin in accordance with an active esterification method or a symmetry anhydride method, instead of the method using the coupler as described above.

Upon completion of the reaction, the resin coupled with the C-terminal amino acid (C-terminal amino acid-resin) is washed once to several times by 2 to 50 ml of a washing solvent with respect to 1 g of the resin which is activated but not couple with the amino acid, i.e., original activated resin. As the washing solvent, for example, at least one solvent of methylene chloride, chloroform, methanol, ethanol, DMF, benzene, and acetic acid can be used. The reaction product is then filtered.

The nonreacted, activated functional groups or amino groups of the washed resin are then blocked for prevention of further reactions, using a terminating reagent and are then washed again. For example, about 0.5 to 5 equivalent weight of the terminating reagent with respect to 1 equivalent weight of the functional group of the resin is added and reacted with the resin for about 10 minutes to 18 hours.

Examples of the terminating reagent are acetic anhydride/TEA/methylene chloride, acetic anhydride/TEA/chloroform, acetylimidazole/DMF, and fluorescamine/diisopropylethylamine/methylene chloride.

Thereafter, the protective group of α-amino group of the C-terminal amino acid-resin is eliminated for coupling with the next amino acid.

For example, trifluoroacetic acid (TFA) is suitable as an elimination reagent for Boc. 100 v/v % TFA or TFA diluted to 10 v/v % or more with methylene chloride, chloroform, or their equivalents can be used, for example, as follows:

About 2 to 50 ml of a TFA solution with respect to 1 g of the original activated resin are preferably added to the C-terminal amino acid-resin and reacted for about 5 to 60 minutes. After the reaction, the reaction mixture is filtered and the C-terminal amino acid-resin washed with the washing solvent. About 2 to 50 ml of a solution of about 5 to 30% TFA in methylene chloride, chloroform, or their equivalents are added with respect to 1 g of the original activated resin to the C-terminal amino acid resin, thereby neutralizing the residual TFA. Thereafter, the reaction product is washed with the washing solvent.

Further, piperidine is suitable as an elimination reagent for Fmoc, and used upon dilution with methylene chloride, DMF, chloroform, or their equivalent to a concentration of 5 to 50%, for example, as follows:

About 2 to 100 ml of the piperidine solution with respect to 1 g of original activated resin are added to the C-terminal amino acid-resin and reacted for about 5 to 60 minutes. After the reaction, the reaction solution is filtered and the C-terminal amino acid-resin washed with the washing solvent.

Then, the fifth amino acid from the N-terminal of the hexapeptide of the present invention (represented by D in the formulas (I) and (II), is coupled to the now free α-amino group of the C-terminal amino acid bonded to the resin, as follows.

The solvent which can swell the resin mentioned above is added to the resultant C-terminal amino acid-resin to suspend it. About 1 to 6 equivalent weight of the protected fifth acid D with respect to 1-equivalent of the functional group on the resin is added to the suspension, and the coupler as described above is then added to the resultant mixture.

The degree of progress of the coupling reaction can be monitored by a ninhydrin reagent or a fluorescamine test. After the reaction, the reaction product is washed with the washing solvent. When the reaction is not completed, the above coupling step is repeated or blocking of excessive α-amino groups of C-terminal amino acids from subsequent reactions is performed using the terminating reagent mentioned above.

Thereafter, elimination of the protection group, washing, neutralization, washing, coupling, and washing are repeatedly performed in the subsequent steps following the same procedures as described above except that each protected amino acid corresponding to each constituent amino acid, is subsequently used, thereby successively condensing the forth amino acid (C) to the first amino acid A to the amino acid moiety on the resin. As a result, a peptide chain corresponding to the hexapeptide of the present invention can be obtained.

(2) Elimination of Peptide Chain from Resin and Elimination of Protective Group

The the resin coupled with the peptide chain (i.e., peptide-resin) is treated with hydrogen fluoride (HF) to cut an amino bond between the peptide and the resin, and at the same time the protective group is eliminated to obtain a free peptide.

A special vessel is required for the HF treatment, and is commercially available.

More specifically, the dried peptide-resin is placed in a vessel, 0.5 to 5 ml of anisole are added thereto with respect to 1 g of peptide-resin to prevent a side reaction, and the mixture is stirred. 2 to 50 ml of a liquid HF are added to the mixture with respect to 1 g of the peptide-resin to treat the peptide-resin at $-20°$ to $0°$ C. for 0.5 to 2 hours. Herein, Dimethylsulfide or ethanedithiol is preferably added to the anisole.

After the reaction, HF is removed at a reduced pressure, and residual HF, a protective group, anisole, and other additives are eliminated by a solvent such as ethyl acetate, diethyl ether, or benzene. The peptide is extracted using an aqueous acidic solution such as an aqueous acetic acid solution, and the resin from which the peptide is eliminated is removed by filtration.

(3) Purification of Crude Peptide

The extract obtained in the above step contains, in addition to the desired peptide, byproducts such as defective peptides formed during the synthesis and must be purified.

More specifically, the extract containing the peptide and the byproducts is concentrated by ultrafiltration. Thereafter, ion exchange, freezing, and drying are performed thereby obtaining a dried product. The dried product is purified by a fractional reverse-phase high-performance liquid chromatography. Finally, ion exchange and gel filtration of a fraction containing the desired peptide are performed to obtain a purified hexapeptide according to the present invention.

Examples of a pharmaceutically acceptably, nontoxic salt of the hexapeptide according to the present invention are salts with an alkali metal such as sodium or potassium or with an alkaline earth metal such as calcium and magnesium, and acid addition salts with an inorganic acid such hydrochloric acid, sulfuric acid, phosphoric acid or carbonic acid, or with an organic acid such as acetic acid propionic acid, tartaric acid succicinic acid, malic acid, asparatic acid or glutamic acid.

The phermaceutically acceptably salt of the hexapeptide according to the present invention also includes a complex salt with a metal compound such as a zinc, a nickel or a cobalt compound, and with a polyamic acid such as poly-L-gultamic acid.

Since the hexapeptide compound according to the present invention directly act on vascular endothelial cells, it is effective and can strongly suppress an edema associated with the increasing vascular permeability. The hexapeptide compound can suppress edemata based on vascular endothelial disorders and various tissue disorders in addition to suppression of a cerebral edema.

The hexapeptide compound according to the present invention has also an anti-endotoxin shock effect, protease inhibition action (an anti-thrombin action, an anti-plasmin action), a hyoptensive action, an anti-DIC action, an anti-allergic action, and a wound healing action.

More particularly, the hexapeptide compound according to the present invention can storlongly suppress the increasing vascular permeability and do not exhibit any side effect around in steroids. Therefore, the hexapeptide compound is useful for diseases such as a cerebral edema, an edema of the lung, an edema of the trachea, a thrombus, an arteriosclerosis, a burn, and a hypertension, and allergic diseases such as a bronchial astham and a pollenosis.

More specifically, the hexapeptide compound according to the present invention is useful as agents for reducing hemorrhage from a sharp trauma such as an injured tissue portion at the time of surgical operation, a lacerated wound of a brain or other tissues caused by a traffic accident and the like, and for relaxing and curing swelling, pain and inflammation caused by the traumata. The hexapeptide compound according to the present invention can also be useful for suppressing internal hemorrhage caused be a dull trauma, and edemata and inflammation which are accompanied with the internal hemorrhage.

The hexapeptide compound according to the present invention also provides excellent effects in suppression and improvement of cerebral edemata by suppressing a leakage of blood components to a tissue matrix found in cerebral ischemetic diseases which include cerebral infractions (e.g., a cerebral thrombus and a cerebral embolism), intracranial hemorrhages (e.g., a cerebral hemorrhage and a subarachnoidal hemorrhage), a transient cerebral ischemic attack, and a acute cerebral blood vessel disorders in a hypertensive encephalopahty.

In addition, the hexapeptide compound according to the present invention provides effects in suppression and improvement of burns, chilblains, other skin inflammations and swelling, an upper tracheal inflammation, an asthma, nasal congestion, a pulmonary edema, and inflammable disorders caused by endogenous and exogenous factors, which directly damage vascular endothelia and mucous membranes, such as an environmental chemical substance, chemotherapeutics of cancer, an endotoxin, and an inflammation mediator.

More specifically, the hexapeptide compound according to the present invention can reduce the hemorrhage, inflammation, swelling and pains of a sharp trauma, i.e., the tissue portion injured by a surgical operation and a traffic accident. The hexapeptide compound also suppresses internal hemorrhage caused by a dull trauma and edemate and inflammation which are accompanied with the internal hemorrhage. In addition, the hexapeptide compound according to the present invention is effective in treatments of cerebral ischemetic diseases which contain cerebral infarctions (e.g., a cerebral thrombus and a cerebral embolism), intracranial hemorrhages (e.g., a cerebral hemorrhage and a subarachnoidal hemorrhage), a transient cerebral ischemic attack, and acute cerebral blood vessel disorders in a hypertensive encephalopathy. In particular, since cerebral edemata are produced during in these acute cerebral blood vessel disorders, suppression of edemata greatly influences the recovery after curing the disease.

The pharmaceutical agent according to the invention, containing a hexapeptide compound as an active ingredient, can be used as a medicine used in therapy of the above-mentioned diseases. The pharmacetical agents of the invention is especially good for an anti-edematous agent, an anti-shock agent, an anti-thrombus agent, an anti-arteriosclerosis agent, an anti-allergic agent, a hypotensive agent, a wound healing agent, and an anti-inflammatory agent.

The hexapeptide compound according to the invention and the pharmaceutical agents can be administered either orally or parenterally in an amount effective for therapy. For adults, the effective amount of the hexapeptide compound of the invention, per day is between 0.1 and 150 nmol/kg. Within this range, the administration amount of the hexapeptide compound should be determined depending on a variety of factors such as degree of disorders, weight of the patient, and age.

The pharmacetical agent of the invention may contain pharmaceutically acceptably diluent or excipient, in the form of liquid, gel, or solid, other than the hexapeptide compounds. Further, if needed, the agent may contain an additive which can be generally used in a drug composition, such as a general antiseptic agent, anti-oxidation agent, or the like.

The pharmaceutical agent of the invention can be used as an oral or parenterally administration drug. The oral administration drug takes the form of, for example, regular tablet, capsule, powder, solution, or suspension, whereas the parenteral administration drug is in the form of, for example, regular solution injection, suspension injection, suppository, or nasal mucosal spray. It should be noted that the agent is preferably administered through intravenous or hypodermic injection. Further, the form of the agent can be selected depending on condition of the patient, age, and degree of disorders.

The present invention will be described in more detail by way of its examples. However, the present invention is not limited by these illustrative examples.

First, examples of the synthesis of the hexapeptide according to the present invention will be describe below.

In the examples, hexapeptide numbers are corresponding hexapeptides shown in Table 1 and 2.

In Table 1 and 2, desamino-Arg represents ω-guanidinopentanic acid. N-acetyl- and N-buthyl- represent acetylated and butylated derivatives of a N-terminal amino acid of the hexapeptide, respectively. —OH represents that a carboxylic group of a C-terminal amino acid is free, —OEt represents that the carboxylic group is converted into an ethylester, and —NH$_2$ represents that the carboxylic group is converted into a carbamoyl. Leucinol is an alcohol form of leucine, i.e., —CH$_2$OH group replaces the carboxylic group of leucine.

(Peptide No. 1=SEQ ID NO:1; Peptide No. 4=SEQ ID NO:4; Peptide No. 6=SEQ ID NO:6; Peptide No. 9=SEQ ID NO:9; Peptide No. 11=SEQ ID NO:11; Peptide No. 14=SEQ ID NO:14; Peptide No. 16=SEQ ID NO:16; Peptide No. 19=SEQ ID NO:19; Peptide No. 21=SEQ ID NO:21; Peptide No. 24=SEQ ID NO:24; Peptide No. 26=SEQ ID NO:26; Peptide No. 29=SEQ ID NO:29; Peptide No. 31=SEQ ID NO:31; Peptide No. 32=SEQ ID NO:32; Peptide No. 33=SEQ ID NO:33; Peptide No. 34=SEQ ID NO:34)

EXAMPLE 1 (Synthesis of Peptide No. 1)

Pretreatment; Activation of Resin 150 g of an organic solvent-insoluble resin (available from Peninsula Lab.; 1% divinylbenzene; 100 to 200 mesh) were placed in a peptide solid-phase synthesis reaction vessel (available from Peninsula Lab.), and the following solvents were added twice each for 5 minutes and stirred and the solvents filtered off, to obtain an activated resin.

(i) Methylene chloride: 1 l
(ii) 10% TEA/methylene chloride: 420 ml

As a washing operation, 1.5 l of methylene chloride, 1.5 l of methanol, and 1.5 l of methylene chloride were added to the activated resin in the order named, and stirred for 2 minutes. The above operation was repeated twice, and the resultant solution was filtered off (this washing operation will be referred to as a washing operation I hereinafter).

TABLE 1

| Peptide No. | Formula |
|---|---|
| 1 | Desamino-Arg—Arg—Pro—Tyr—Ile—Leu—OH |
| 2 | Desamino-Arg-D-Arg—Pro—Tyr—Ile—Leu—OH |
| 3 | Desamino-Arg-D-Lys—Pro—Tyr—Ile—Leu—OH |
| 4 | Desamino-Arg—Arg—Pro—Trp—Ile—Leu—OH |
| 5 | Desamino-Arg—Arg—Pro-D-Trp—Ile—Leu—OH |
| 6 | Desamino-Arg—Arg—Pro—Tyr—Ile—(NCH$_3$)Leu—OH |
| 7 | Desamino-Arg-D-Lys—Pro—Trp—Ile—Leu—OH |
| 8 | Desamino-Arg-D-Lys—Pro—Tyr—Ile—(NCH$_3$)Leu—OH |
| 9 | Desamino-Arg—Arg—Pro—Trp—Ile—(NCH$_3$)Leu—OH |
| 10 | Desamino-Arg-D-Lys—Pro—Trp—Ile—(NCH$_3$)Leu—OH |
| 11 | Desamino-Arg—Arg—Pro—Tyr—Ile—Leu—OEt |
| 12 | Desamino-Arg-D-Arg—Pro—Tyr—Ile—Leu—OEt |
| 13 | Desamino-Arg-D-Lys—Pro—Tyr—Ile—Leu—OEt |
| 14 | Desamino-Arg—Arg—Pro—Trp—Ile—Leu—OEt |
| 15 | Desamino-Arg—Arg—Pro-D-Trp—Ile—Leu—OEt |

TABLE 2

| Peptide No. | Formula |
|---|---|
| 16 | Desamino-Arg—Arg—Pro—Tyr—Ile—(NCH$_3$)Leu—OEt |
| 17 | Desamino-Arg-D-Lys—Pro—Trp—Ile—Leu—OEt |
| 18 | Desamino-Arg-D-Lys—Pro—Tyr—Ile—(NCH$_3$)Leu—OEt |
| 19 | Desamino-Arg—Arg—Pro—Trp—Ile—(NCH$_3$)Leu—OEt |
| 20 | Desamino-Arg-D-Lys—Pro—Trp—Ile—(NCH$_3$)Leu—OEt |
| 21 | Desamino-Arg—Arg—Pro—Tyr—Ile-Leucinol |
| 22 | Desamino-Arg-D-Arg—Pro—Tyr—Ile-Leucinol |
| 23 | Desamino-Arg-D-Lys—Pro—Trp—Ile-Leucinol |
| 24 | Desamino-Arg—Arg—Pro—Trp—Ile-Leucinol |
| 25 | Desamino-Arg—Arg—Pro-D-Trp—Ile-Leucinol |
| 26 | Desamino-Arg—Arg—Pro—Tyr—Ile—(NCH$_3$)Leusinol |
| 27 | Desamino-Arg-D-Lys—Pro—Trp—Ile-Leucinol |
| 28 | Desamino-Arg-D-Lys—Pro—Tyr—Ile—(NCH$_3$)Leucinol |
| 29 | Desamino-Arg—Arg—Pro—Trp—Ile—(NCH$_3$)Leucinol |
| 30 | Desamino-Arg-D-Lys—Pro—Trp—Ile—(NCH$_3$)Leucinol |
| 31 | N-acetyl—Arg—Arg—Pro—Tyr—Ile-Leucinol |
| 32 | N-acetyl—Arg—Arg—Pro—Tyr—Ile—Leu—NH$_2$ |
| 33 | N-buthyl—Arg—Arg—Pro—Tyr—Ile—Leucinol |
| 34 | N-buthyl—Arg—Arg—Pro—Tyr—Ile—Leu—NH$_2$ |

Step 1; Coupling Amino acid to Resin

The following materials were added in turn to the whole of the resin obtained in the pretreatment and was stirred, and the resultant mixture was filtered.

(1) DMF: 1.5 l
(2) Boc-Leu.H₂O: 38.2 g
(3) 1M DCC/DMF—CH₂Cl₂: 120 ml (stirring for 20.0 hours)

Herein, Boc- represents that the α-amino group of an amino acid is protected by a protective group Boc.

Subsequently, the washing operation I was performed.

The result of a ninhydrin test of the treated resin exhibited negative.

Step 2; Elimination of Protective group

The following solvent was added to the whole of the resin obtained in step 1, and the mixture was stirred and filtered.

50% TFA/methylene chloride (stirring for 5 and 25 minutes, each for 1.8 l)

Subsequently, the washing operation I was performed.

Steps 3-7; Extension of Peptide chain

To the whole of the resin obtained in the step 2, coupling of amino acids, elimination of protective groups, neutralization, and washing were performed following the same procedures as in steps 1 and 2 except that amino acids protected by protective groups (protected amino acids) shown in Table 3 below were sequentially coupled to the Leu on the resin using coupler under coupling conditions shown in Table 3.

In Table 3, HOBt represents 1-hydroxybenzotriazole.

TABLE 3

| | | Coupling Condition | | | |
|---|---|---|---|---|---|
| Step | Protected Amino Acid | Amount Used (g) | Solvent | Time (h) | Coupler |
| 3 | Boc—Ile.½H₂O | 72.0 | CH₂Cl₂ | 16.0 | DCC |
| 4 | Bod—Tyr(Br-Z) | (1) 237.2 | CH₂Cl₂ | 17.0 | DCC |
| | | (2) 100.0 | DMF | 44.0 | DCC + HOBT |
| 5 | Boc—Pro | (1) 64.5 | DMF | 13.5 | DCC + HOBT |
| | | (2) 25.0 | CH₂Cl₂ | 3.0 | DCC |
| 6 | Boc—Arg(Tos) | 43.0 | CH₂Cl₂ | 20.0 | DCC |
| 7 | Desamino-Arg(Tos) | 43.0 | CH₂Cl₂ | 20.0 | DCC |

After coupling of Desamino-Arg and washing in step 7 were completed, a peptide-resin was removed from the reaction vessel and was dried.

Deamination of Arg used in step 7 was performed as following. First, 0.1 mol of 5-aminovaleric acid hydrochloride was dissolved in 50 ml of a 2N-sodium hydroxide solution. 0.1 mol of S-methylthiocarbamide was added thereto, and the resultant solution was stirred and reacted at room temperature for 2 days. The reaction mixture was concentrated and purified by a column chromatography. The purified product was converted to hydrochloride. The Desamino-Arg hydrochloride obtained as described above used in step 7.

Step 8; Elimination of Peptide from Resin and Elimination of Protective Group 4 g of the peptide-resin obtained in step 7 were placed in a HF reaction vessel, and 4 ml of anisole and 1 ml of methylsulfide were added thereto and stirred. Thereafter, the HF reaction vessel set in an HF reaction apparatus (available from Peptide Lab.) The HF reaction vessel was cooled in a dryice-acetone bath, and about 35 ml of HF were charged thereto. The contents of the vessel was stirred and reacted while cooling in an ice water bath for 45 minutes. After completion of the reaction, HF was distilled off by a vacuum pump for 15 minutes. After the HF reaction vessel was removed from the ice water bath to a water bath, evacuation of HF was continued for 15 minutes.

Ether was added to the solution, and the resultant solution was stirred well and filtered using a glass filter. The product remaining on the filter was washed with ether (a total of about 300 ml), and a peptide eliminated from the resin was extracted four times using 100 ml of a 0.1N aqueous acetic acid solution.

Step 9; Purification

The pH of the extract obtained in step 8 was adjusted to 5.0 by acetic anhydride, and filtered using an ultrafiltration membrane having a molecular weight of 1,000. The resultant solution was subjected to a column of a cation exchange resin (available from Whatman). Using an ammonium acetate buffer as a mobile phase, the component absorbed on the resin was eluted. The eluted component was freeze-dried.

The dried product was purified by a fractional reverse-phase high-performance liquid chromatography. In this chromatography, use was made of an ODP-90 (available from ASAHI CHEMICAL INDUSTRY CO., LTD.) as the column and a phosphate buffer/acetonitrile mixed solvent as gradient eluent.

A main peak fraction obtained by the above chromatography was concentrated by the ultrafiltration membrane as mentioned above. The obtained concentrate was subjected to column of cation exchange resin SP-Sephadex (available from Pharmacia Fine Chemicals, Inc.). Using an aqueous sodium chloride solution as a mobile phase, the component adsorbed on the resin was eluted. The eluted component was subjected to again a column of Sephadex G-25 (available from Pharmacia Fine Chemicals, Inc.). Thereafter, using an aqueous acetic acid solution as a mobile phase, the component adsorbed on the resin was eluted, and was freeze-dried. The resultant product exhibited a single spot by a thin layer chromatography using three developing solvents and electromigration (Whatman 3MM, pH 3.5; 1,500 V. 1 hr.).

The amino acid analysis of the purified product is summarized as follows. Values within the parentheses represent theoretical values.

Example 1 (Peptide No. 1)

Arg: 0.89 (1); Pro: 1.02 (1);
Tyr: 0.98 (1); Ile: 0.97 (1);
Leu: 1.01 (1); Desamino-Arg NH₃: - (1)

The result of the amino acid analysis supported that the purified product obtained by the above method was the peptide No. 1 having the amino acid composition shown in Table 1 above.

EXAMPLES 2–10 (Synthesis of of Peptide Nos. 2–10)

Hexapeptides of samples having peptide Nos. 2 to 10 were synthesized and purified following the same procedures as in Example 1 except that the starting amino acids were changed to the protected amino acids corresponding to the peptide compositions shown in Table 1.

The results of amino acid analysis of the purified products are shown below. Values within parentheses represent theoretical values.

Example 2 (Peptide No. 2)

Arg: 0.96 (1); Pro: 1.01 (1);
Tyr: 0.96 (1); Ile: 0.98 (1);
Leu: 1.03 (1); Desamino-Arg $NH_3$: - (1)

Example 3 (Peptide No. 3)

Arg: 1.04 (1); Lys: 0.96 (1);
Pro: 0.94 (1); Tyr: 0.97 (1);
Ile: 1.02 (1); Leu: 0.98
Desamino-Arg $NH_3$: (1)

Example 4 (Peptide No. 4)

Arg: 0.96 (1); Pro: 0.97 (1);
Trp: 0.94 (1); Ile: 0.98 (1);
Leu: 1.02 (1); Desamino-Arg $NH_3$: - (1)

Example 5 (Peptide No. 5)

Arg: 0.93 (1); Pro: 0.96 (1);
Trp: 0.96 (1); Ile: 1.01 (1);
Leu: 0.97 (1); Desamino-Arg $NH_3$: - (1)

Example 6 (Peptide No. 6)

Arg: 1.03 (1); Pro: 0.98 (1);
Tyr: 1.02 (1); Ile: 0.98 (1);
Leu: 1.02 (1); $NCH_3$: present (1);
Desamino-Arg $NH_3$: - (1)

Example 7 (Peptide No. 7)

Arg: 1.03 (1); Lys: 0.94 (1);
Pro: 1.01 (1); Trp: 0.97 (1);
Ile: 0.97 (1); Leu: 0.97 (1);
Desamino-Arg $NH_3$: - (1)

Example 8 (Peptide No. 8)

Arg: 1.02 (1); Lys: 0.97 (1);
Pro: 1.04 (1); Tyr: 0.97 (1);
Ile: 1.01 (1); Leu: 0.97 (1);
$NHCH_3$: present (1);
Desamino-Arg $NH_3$: - (1)

Example 9 (Peptide No. 9)

Arg: 0.95 (1); Pro: 0.97 (1);
Trp: 1.02 (1); Ile: 0.98 (1);
Leu: 0.99 (1); $NCH_3$: present (1);
Desamino-Arg $NH_3$: (1)

Example 10 (Peptide No. 10)

Arg: 0.98 (1); Lys: 1.03 (1);
Ile: 0.96 (1); Leu: 1.01 (1);
$NHCH_3$: present (1);
Desamino-Arg $NH_3$: (1)

Herein, "$NCH_3$" represent a peptide bond whose hydrogen atom was substituted by methyl group (The same applies below).

These results of amino acid analysis supported that the purified products obtained by the above method were peptides Nos. 2 to 10 each having the amino acid composition shown in Table 1.

EXAMPLES 11–20 (Synthesis of Peptides Nos. 11–20)

For converting a carboxylic group of a C-terminal amino acid into an ethylester, first, each peptide-resin (500 mg) obtained by sequentially condensing source amino acids by the same procedures as Example 1 was suspended in 1N TEA/ethanol (50 ml), and the resultant mixture was stirred at room temperature for 17 hours. The resultant mixture was filtered and the resin was washed with ethanol. The filtrate and the washing solution were collected and concentrated at a reduced pressure. The resultant crude products were purified as in of Example 1.

Results of amino acid analysis of the purified products are shown below. Values within the parentheses represent theoretical values.

Example 11 (Peptide No. 11)

Arg: 0.97 (1); Pro: 1.04 (1);
Tyr: 1.02 (1); Ile: 0.96 (1);
Leu: 0.97 (1); Desamino-Arg $NH_3$: - (1)

Example 12 (Peptide No. 12)

Arg: 0.98 (1); Pro: 0.97 (1);
Tyr: 0.95 (1); Ile: 0.97 (1);
Leu: 1.01 (1); Desamino-Arg $NH_3$: - (1)

Example 13 (Peptide No. 13)

Lys: 0.97 (1); Pro: 1.02 (1);
Tyr: 0.98 (1); Ile: 1.03 (1);
Leu: 0.97 (1); Desamino-Arg $NH_3$: (1)

Example 14 (Peptide No. 14)

Arg: 0.97 (1); Pro: 0.98 (1);
Trp: 1.01 (1); Ile: 0.97 (1);
Leu: 0.99 (1); Desamino-Arg $NH_3$: (1)

Example 15 (Peptide No. 15)

Arg: 1.03 (1); Pro: 1.04 (1);
Trp: 0.98 (1); Ile: 1.03 (1);
Leu: 0.97 (1); Desamino-Arg $NH_3$: (1)

Example 16 (Peptide No. 16)

Arg: 0.97 (1); Pro: 0.96 (1);
Tyr: 1.02 (1); Ile: 0.97 (1);
Leu: 1.03 (1); Desamino-Arg $NH_3$: (1)

Example 17 (Peptide No. 17)

Lys: 1.02 (1); Pro: 1.01 (1);
Trp: 0.97 (1); Ile: 1.04 (1);
Leu: 0.96 (1); Desamino-Arg $NH_3$: (1)

Example 18 (Peptide No. 18)

Lys: 0.96 (1); Pro: 0.98 (1);
Tyr: 1.02 (1); Ile: 0.97 (1);
Leu: 0.99 (1); $NCH_3$: present (1);
Desamino-Arg $NH_3$: - (1)

Example 19 (Peptide No. 19)

Arg: 0.98 (1); Pro: 1.04 (1);
Trp: 1.02 (1); Ile: 0.99 (1);

Leu: 1.03 (1); NCH$_3$: present (1);
Desamino-Arg NH$_3$: - (1)

Example 20 (Peptide No. 20)

Lys: 1.02 (1); Pro: 0.98 (1);
Trp: 1.03 (1); Ile: 0.97 (1);
Leu: 0.97 (1); NCH$_3$: present (1);
Desamino-Arg NH$_3$: - (1)

These results of amino acid analysis supported that the purified products obtained by the above method were peptides Nos. 11 to 20 each having the amino acid composition shown in Table 1 or 2.

EXAMPLES 21-30 (Synthesis of Peptides Nos. 21-30)

Five amino acids corresponding to each of peptides Nos. 21 to 30, other than leucinol, were sequentially condensed by the same procedures as in Example 1. The synthesized peptide chains each consisting of the five amino acids were eliminated from the resins according to the same procedures as in Example 1.

In order to protect an α-amino group of an N-terminal amino acid of each peptide chain by Boc, each peptide chain (0.02 mol) was dissolved in a solvent mixture of 30 ml of water and 30 ml of dioxane, and sodium bicarbonate (0.048 mol) and Boc-N$_3$ (0.024 mol) were added thereto. The resultant solution was stirred and reacted at 40° to 45° C. for 24 hours.

After the reaction, the reaction mixture was concentrated at a reduced pressure, 50 ml of water were added thereto, and the resultant mixture was washed with 50 ml of ethyl acetate. The water layer was collected, and 70 ml of 0.5M citric acid were added thereto with icing. Sodium chloride was added to the resultant solution to be saturated. The reaction product was extracted with 100 ml ethyl acetate three times and was then dried with sodium sulfate. The dried product was concentrated at a reduced pressure.

The peptide chains (0.005 mol) was dissolved in 10 ml of THF, and 0.45 ml of N-methylformate and 0.35 ml of ethyl chlorocarbonate were added thereto while the solution was cooled to −20° C. After a lapse of 5 minutes, 5 ml of a DMF solution containing leucinol hydrochloride (0.005 mol) and N-methylformate (0.45 ml) were added to the above solution, and the resultant mixture was stirred and reacted at −70° C. for 2 hours. As result, leucinol was condensed to the peptide chain.

After the reaction, the precipitant was filtered off, and the filtrate was concentrated, dried, and solidified. Thereafter, 50 ml of ethyl acetate were added to the solid body to dissolve the solid body, and the mixture was sequentially washed with 50 ml of 5% sodium bicarbonate two times and 50 ml of distilled water three times. The washed ethyl acetate ester layer was concentrated and solidified, and the protective group was eliminated by the same procedure as in Example 1. The crude product thus obtained was purified by HPLC to obtain each desired hexapeptide.

Results of amino acid analysis of the purified products are shown below. Values within the parentheses represent theoretical values.

Example 21 (Peptide No. 21)

Arg: 2.02 (2); Pro 0.97 (1);
Tyr: 1.02 (1); Ile: 0.98 (1);
Leucinol: - (1)

Example 22 (Peptide No. 21)

Arg: 1.98 (2); Pro: 1.04 (1);
Tyr: 0.96 (1); Ile: 1.02 (1);
Leucinol: - (1)

Example 23 (Peptide No. 23)

Arg: 0.95 (1); Lys: 0.97 (1);
Pro: 0.99 (1); Tyr: 0.96 (1);
Ile: 1.02 (1); Leucinol: - (1)

Example 24 (peptide No. 24)

Arg: 2.05 (2); Pro: 0.98 (1);
Trp: 1.02 (1); Ile: 0.97 (1);
Leucinol: - (1)

Example 25 (Peptide No. 25)

Arg: 1.97 (2); Pro: 1.03 (1);
Trp: 0.98 (1); Ile: 1.02 (1);
Leucinol: - (1)

Example 26 (Peptide No. 26)

Arg: 2.04 (2); Pro: 0.98 (1);
Tyr: 1.02 (1); Ile: 0.96 (1);
Leucinol: - (1); NCH$_3$: present

Example 27 (Peptide No. 27)

Arg: 1.04 (1); Lys: 1.03 (1);
Pro: 0.97 (1); Trp: 0.98 (1);
Ile: 0.97 (1); Leucinol: - (1)

Example 28 (Peptide No. 28)

Arg: 1.02 (1); Lys: 0.98 (1);
Pro: 1.02 (1); Tyr: 1.01 (1);
Ile: 1.05 (1); Leucinol: - (1);
NCH$_3$: present

Example 29 (Peptide No. 29)

Arg: 2.03 (2); Pro: 1.02 (1);
Trp: 0.98 (1); Ile: 0.96 (1);
Leucinol: - (1)

Example 30 (Peptide No. 30)

Arg: 1.02 (1); Lys: 0.97 (1);
Pro: 0.96 (1); Trp: 1.01 (1);
Ile: 0.97 (1); Leucinol: - (1);
NCH$_3$: present These results of amino acid analysis supported that the purified products obtained by the above method were peptides Nos. 21 to 30 each having the amino acid composition shown in Table 2.

EXAMPLE 31 (Peptide No. 31)

Five amino acids corresponding to peptide No. 31, other than leucinol, were sequentially condensed on the resin by the synthesis method following the same procedures as in Example 21. Thereafter, an acetyl group was introduced into an N-α-amino group of the peptide chains thus obtained, by a known method.

The synthesized peptide chain was eliminated from the resin, and the protective group was eliminated from the peptide chain as in Example 1. The resin was washed with a washing solvent. The washing solution and the filtrate were concentrated and the obtained concentrate was freeze-dried. The α-amino group of the peptide chain contented in dried product was protected with a Boc. Leucinol was then condensed to the peptide chain, and the protective group was eliminated from the hexapeptide thus obtained. The crude product was purified with HPLC.

A result of amino acid analysis of this purified product is shown below. Values within parentheses represent theoretical values.

Arg: 1.99 (2); Pro: 1.02 (1);
Tyr: 0.91 (1); Ile: 0.99 (1);
Leucinol: - (1)

Mass analysis of this hexapeptide was performed by an fast atom bombardment mass spectrometry (FAB). As a result, a molecular ions peak of m/z=846 was observed, thereby confirming that synthesis of the target hexapeptide was completed.

EXAMPLE 32 (Peptide No. 32)

Using a benzohydrylamine (BHA) resin support or a paramethylbenzhydrylamine (MBHA) resin support, amino acids corresponding to the peptide No. 32 were sequentially condensed in the resin following the same procedures as in Example 1. Upon completion of the synthesis, the N-terminal amino acid was acetylated, the peptide chain thus obtained was eliminated from the resins, and the protective group was eliminated from the peptide chain.

A result of amino acid analysis of this purified product is shown below. Values within the parentheses represent theoretical values.

Arg: 2.02 (2); Pro: 0.99 (1);
Tyr: 1.03 (1); Ile: 0.97 (1);
Leu: 1.06 (1); NH$_3$: 1.12 (1)

The result supported the resultant product obtained by the above method was peptide No. 32 having the amino acid composition shown in Table 2.

EXAMPLE 33 (Peptide No. 33)

Five amino acids corresponding to the peptide No. 33, other than leucinol, were sequentially condensed by the synthesis method following the same procedures as in Example 31, and a butyl group was introduced into an N-α-amino group of the N-terminal amino acid by a known method using butyl chloride. Leucinol was condensed by the method following the same procedures as in Example 31, the protective group was eliminated from the peptide chain thus obtained, and the crude product containing the hexapeptide was purified with HPLC.

A result of amino acid analysis of this purified product is shown below. Values within the parentheses represent theoretical values.

Arg: 1.97 (2); Pro: 0.96 (1);
Tyr: 1.04 (1); Ile: 0.98 (1);
Leucinol: - (1)

The result supported the resultant product obtained by the above method was peptide No. 33 having the amino acid composition in Table 2.

EXAMPLE 34 (Peptide No. 34)

Amino acids corresponding to the peptide No. 34 were sequentially condensed following the same procedures as in Example 32. Upon completion of the synthesis, a butyl group was introduced to an N-terminal amino acid by a known method. The obtained peptide chain was eliminated from the resin, and the protective group was eliminated from the peptide chain in accordance with the method following same procedures as in Examples 32. The crude product containing the hexapeptide was purified with HPLC.

A result of amino acid analysis of this purified product is shown below. Values within the parentheses represent theoretical values.

Arg: 2.03 (2); Pro: 0.98 (1);
Tyr: 0.94 (1); Ile: 0.98 (1);
Leu: 1.01 (1); NH$_3$: 1.09 (1)

Mass analysis of this peptide was performed by FAB, and molecular ions peak of m/z=871.5 was observed, thereby confirming that synthesis of the desired hexapeptide was completed.

Pharmacological Effect Test

In order to confirm an increasing vascular permeability suppression action, a vascular endothelial disorder amelioration action an anti-edematous action, an anti-inflammatory action, an anti-shock action, an anti-DIC action, a protease inhibition action, anti-allergic action a hypotensive action, and a wound healing action of the hexapeptide compound according to the present invention, the following experimental examples 1 to 8 were performed.

Experimental Example 1: Vascular Permeability Acceleration Suppression Action After 6-week male Sprague-Dawley (SD) rats (each group consisted of 10 rats) were fed for a week, they were used in this experiment.

The concentrations of samples of the hexapeptides (peptide Nos. 1 to 30) were dissolved by an acetic acid buffer solution added with a 1% bovine serum albumin (BSA).

An aliqrot of 1 ml/kg of each of the peptides Nos. 1 to 30 was injected into the femoral vein of the right leg of each rat anesthetized with 50 mg/kg of Nembutal Sodium (available from Dainippon Pharmaceutical Co., Ltd.). After 10 minutes, the nontreated left leg of the rat was dipped in 58° C. hot water for one minute to form an edema. Each rat was left at room temperature for 29 minutes, and the volumes of both legs of each rat were measured. As a control, the experiment following the same procedure as describe above was performed except that 1 ml/kg of a sodium acetate buffered solution containing 1% BSA instead of the hexapeptide of the present invention was injected in rats.

A rate (%) of increase in leg volume was calculated from the result of the above measurement by equation (1) below:

$$\text{Rate of Increase in Leg Volume (\%)} = \frac{\text{(Heated Leg Volume)} - \text{(Non-heated Leg Volume)}}{\text{(Heated Leg Volume)}} \times 100 \quad (1)$$

The rates were compared with that of the control.

The results are summarized as suppression rates (%) obtained by equation (2) shown in Table 4.

TABLE 4

| Peptide No. | Suppression Rate (%) | Petide No. | Suppression Rate (%) |
|---|---|---|---|
| 1 | 81.6 | 2 | 77.4 |
| 3 | 70.8 | 4 | 66.3 |
| 5 | 61.4 | 6 | 53.9 |
| 7 | 54.6 | 8 | 58.7 |
| 9 | 59.4 | 10 | 54.1 |
| 11 | 22.8 | 12 | 20.4 |
| 13 | 19.6 | 14 | 17.5 |
| 15 | 14.2 | 16 | 19.1 |
| 17 | 11.9 | 18 | 18.2 |
| 19 | 20.8 | 20 | 19.4 |
| 21 | 19.7 | 22 | 16.9 |
| 23 | 20.8 | 24 | 24.1 |
| 25 | 19.6 | 26 | 14.3 |
| 27 | 18.2 | 28 | 15.4 |

TABLE 4-continued

| Peptide No. | Suppression Rate (%) | Petide No. | Suppression Rate (%) |
|---|---|---|---|
| 29 | 17.9 | 30 | 12.6 |

$$\text{Suppression rate (\%)} = \frac{X_o - X}{X_o} \times 100 \quad (2)$$

X: rate of increase in leg volume (%) of the present invention.

Xo: rate of increase in leg volume (%) of the control

As shown in Table 4, the peptides Nos. 1 to 30 were confirmed to have a vascular permeability acceleration suppression action and could suppress edemata.

An action of the hexapeptide compounds according to the present invention for suppressing the increasing vascular permeability is a lowering of a permeability of vascular endothelial cells to close a gap between the vascular endothelial cells. In arteriosclerotic diseases as shown in a hypercholesterolemia model of a monkey proposed by R. Ross (pp. 103-108, 1990, Elsevier Science Publisher B.V., Netherlands), monocytes, T-lymphocytes, and denatured cholesterols are attached to the gaps between the vascular endothelial cells and intrude under the vascular endothelial cells through the gaps, thereby finally forming fatty spots as an initial change in morbid state in an arteriosclerosis. The vascular endothelial cells are thinned with an increase in fatty spots and are finally separated and open. Thereafter, most of foamy cells flow out, and platelets are attached to cause a thrombus. Smooth muscle cells are grown by a PDGF (Platelet-Derived Growth Factor) produced from the platelets, and the wall thickness of the artery is increased to result in an arteriosclerosis.

When the gap between the vascular endothelial cells is reduced by a hexapeptide according to the present invention, invasion of a low-density lipoprotein (LDL) and monocytes below the vascular endothelial cells can be prevented. Hence, the arteriosclerosis can be prevented.

Experimental Example 2: Anti-Shock Action

In this experiment, male ICR mice (each group consisted of 10 mice) each having a weight of 25 g to 35 g were used. Each of peptides Nos. 1, 31 and 32 was dissolved in a sodium acetate buffered solution (pH 6.0) added with 1% BSA or in a physiological saline.

An endotoxin to induce a shock was obtained by dissolving Lipopolysaccharide [E. coli; 0127B8 (Difco)] in a physiological saline.

Each of peptialdes Nos. 1, 31 and 32 was intravenously injected at a by dose of 5 ml/kg to each mouse, and the endotoxin with concentration of 10 mg/kg was intravenously injected at a dose of 5 ml/kg after 10 minutes. The lethal rates (%) of these mice within 24 hours were measured. As a control, 5 ml/kg of the sodium acetate buffered solution added with 1% BSA was injected instead of the hexapeptide of the present invention.

The results are summarized in Table 5.

TABLE 5

| Peptide No. | Dose | Lethal rate within 24 hours (%) |
|---|---|---|
| Control | — | 80 |
| 1 | 32 nmol/kg × 4 | 20 |
| 31 | 32 nmol/kg × 4 | 10 |
| 32 | 32 nmol/kg × 4 | 20 |

In this experiment, a septic shock is a major cause of death of the mouse. The septic shock is an acute circulatory disorder which exhibits a shock state such that a vascular endothelial disorder occurs by bacterial infection by means of an endotoxin serving as a bacterial cell wall component, and increasing vascular permeability is to cause leakage of blood components outside the blood vessel.

Thus, as shown in Table 5, it is apparent that the peptides Nos. 1, 31 and 32 according to the present invention can suppress the increasing vascular permeability, and it was confirmed that they are useful as antishock drugs.

Experimental Example 3: Anti-Edematous tous Action

In this experiment, 8-week male Wistar rats were used, and peptides Nos. 1, 31 and 32 dissolved in a saline added with 1% BSA were used.

Iron column whose diameter was 5 mm cooled by dryice acetone was placed on the left epidural portion of each rat to cause a vascular cerebral edema. Freezing was performed to form an injured portion after an hour, and the brain of each rat was taken out. The brain was divided into right and left cerebral cortices, and weights of the left cerebral cortices were measured. The left cerebral cortices was dried at 105° C. for 24 hours, and weights of the dried left cerebral cortices were measured to obtain water contents (%). In this operations, the peptides Nos. 1, 31 and 32 were intravenously injected at the concentration shown in Table 6 to each rat 10 minutes before and 20 minutes after the freezing. As a control, 1 ml/kg of the saline added with 1% BSA instead of the peptides was injected into rat according to same procedures as described above.

The results are summarized in Table 6.

TABLE 6

| Peptide No. | Dose | Water Content (%) |
|---|---|---|
| Control | — | 81.4 |
| 1 | 32 nmol/kg | 81.2 |
| 31 | 32 nmol/kg | 80.8 |
| 32 | 32 nmol/kg | 80.6 |

As shown in Table 6, the peptides Nos. 1, 31 and 32 according to the present invention were confirmed to have the increasing vascular permeability suppression action and suppress the edemata.

Experimental Example 4: Hypotentsive Action

Hybrid grown-up dogs (each group consisted of six dogs) were used in this experiment. Peptide No. 1 was dissolved in a sodium acetate buffered solution added with a 1% BSA. 25 mg/kg of sodium pentobarbital were intravenously injected to each dog. A blood pressure of the femoral artery and a blood flow rate of the ascending aorta of each dog were measured while performing the artificial respiration. 2 nmol/kg of peptide No. 1 was intravenously injected. Thereafter, the blood pressure and the blood flow were measured again.

As a result, in the peptide No. 1, although the average blood pressure before the hexapeptide injection was 84 mmHg, the average blood pressure after the peptide injection was decreased to 48 mmHg.

The blood flow rate was decreased from 0.95 l/min to 0.75 l/min by the injection.

The hexapeptide compounds according to the present invention have a hypotensive action and can serve as useful as hypotensive agent by reducing the resistance in peripheral blood vessels.

Experimental Example 5: Anti-DIC Action

Hybrid grown-up dogs (each group consisted of six dogs) were used in this experiment. 30 mg/kg of pentobarbital were intravenously injected to anesthetize each dog. Intravenous injection of 32 nmol/kg of each of peptides Nos. 1, 31 and 32 was performed. After 30 minutes, 3 mg/kg of an endotoxin derived from *Escherichia Coli* were intravenously injected while the artificial respiration was performed with air.

Samples of blood were collecting from each dog immediately before the injection of the peptides and 120 minutes after the injection of the endotoxin.

As a control, a experiment was performed according to same procedure as described above except that the hexapeptides was not injected.

The results are summarized in Table 7. The number of platelets is the number per 1 mm$^3$ (1 μl) of the blood in Table 7.

TABLE 7

| Peptide No. | Average Number of Platelets Immediately before Injection Endotoxin | Average Number of Platelets 120 Minutes after Venous Injection of Endotoxin |
|---|---|---|
| Control | 72 × 10$^4$ | 43 × 10$^4$ |
| 1 | 68 × 10$^4$ | 61 × 10$^4$ |
| 31 | 70 × 10$^4$ | 64 × 10$^4$ |
| 32 | 71 × 10$^4$ | 58 × 10$^4$ |

As is apparent from the above results, the hexapeptides according to the present invention were confirmed to suppress a blood coagulation acceleration state and a decrease in the number of platelets.

Experimental Example 6: Protease Inhibition Action

Each of peptides Nos. 1, 31 to 34 was mixed at various volume with thrombin (final conc. 10 U/ml), and the resultant mixture was preincubated at 37° C. for 5 minutes. A synthetic coloring base (Test Team$^R$ S-2238 available from Daiichi Kagaku Yakuhin) was added to the above preincubated mixture and was reacted at 37° C. for 15 minutes.

2% citric acid was added to the above mixture to stop the reaction. Hydrolysis was performed using residual thrombin, and free p-nitroaniline removed from the synthetic coloring base was subjected to colorimetric determination at a wavelength of 405 nm, thereby obtaining the inhibition capability with reference to 0.1M tris buffer. On the base of the inhibition capability thus obtained, a concentration of the peptides when each peptide inhibited the activity of thrombin with 50%, i.e. IC$_{50}$ was calculated.

The results are summarized in Table 8.

TABLE 8

| Peptide No. | IC$_{50}$ Value (μM) |
|---|---|
| 1 | 2.5 |
| 31 | 2.3 |
| 32 | 2.2 |
| 33 | 2.3 |
| 34 | 2.2 |

As is apparent from the above results, the hexapeptide compounds according to the present invention were confirmed to have an anti-thrombin action as an inhibition action against a protease.

Experimental Example 7: Anti-allergic Action

In this experiment, 6-week, male Wister rats (each group consisted of 10 rats) were used, and the back of these rats were shaved.

An anti-egg albumin rat serum was diluted with a saline to forty-fold of its volume, thereby obtaining an anti-egg albumin rat serum solution. 1 ml of the anti-egg albumin rat serum solution was intradermally injected to both side parts against the median line in the shaved portion, thereby sensitizing passively the rats. After 48 hours, 1 ml of a 0.5% Evans blue solution containing 10 mg of a egg-albumin was intravenously injected to the each rat, thereby provocating a passive cutaneous anaphylaxis (PCA) reaction.

After 30 minutes, the rats were decapitated, thereby subjecting to hemorrhage to death. The skins were peeled from the rats, and a long diameter and a short diameter of a blue stained portions caused by the PCA reaction in each rat were measured, and area of the blue-stained portions were calculated on the base of the obtained data.

In these operations, the of peptides Nos. 1, 31 and 32 were dissolved in a sodium acetate buffered solution containing 1% BSA and was intravenously injected to each rat at 10 minutes before the provocation of the PCA reaction. As a control, the sodium acetate buffer solution containing 1% BSA instead of the peptide solutions was injected according to same procedure as described above.

The results are summarized in Table 9.

TABLE 9

| Peptide No. | Dose | Area of blue-stained portion (mm$^2$) |
|---|---|---|
| Control | — | 188.3 ± 9.71 |
| 1 | 32 nmol g/kg | 80.2 ± 3.76 |
| 31 | 32 nmol g/kg | 141.5 ± 7.96 |
| 32 | 32 nmol g/kg | 112.8 ± 4.83 |

As shown in Table 9, the hexapeptide compounds according to the present invention were confirmed to have an anti-allergic action, and were useful for an anti-allergic agent.

Also, the hexapeptide compounds according to the present invention were useful for an anti-inflammatory agent, since the inflammatory originates in the disorders of the vascular endothelim and the tissular mucous membranes caused by e.g., various parameters, which were eliminated by the increasing vascular permeability suppression.

Experimental Example 8: Wound Healing Action

The male SD rats (each group consisted of 10 rats) were anesthetized with ether and shaved in the back of the each rat, and the anesthetized portion was formed by a length of 30 mm along the median line by using a degreased, sterilized razor blade. The wound was immediately sutured at three equidistant positions, and the stitches were taken out after three days. The rats were subjected to hemorrhage to death in the eighth day, and the skins were peeled from the rats.

A skin stripe having a size of 1 cm × 4 cm was formed from a wounded portion of each rat. Both ends of this stripe were set in a wound curing measurement tensile test instrument (TK-251 available from Unicom), and a tensile force (traction tension: g/cm) required to cut the wound portion was measured.

Each hexapeptide compound according to the present invention was dissolved in an acetic acid buffer solution added with 1% BSA and was intravenously injected to each rat for 8 days (once a day) from the date of wound formation. As a control, 1 ml/kg of the sodium acetat buffered solution added with 1% BSA instead of the hexapeptide solutions was injected according to same procedure as described above.

The results are summarized in Table 10.

TABLE 10

| Peptide No. | Dose (nmol/kg) | Traction Tension (g/cm) |
|---|---|---|
| Control | — | 456.2 ± 21.6 |
| 1 | 32 | 545.7 ± 31.2 |
| 31 | 32 | 539.2 ± 27.7 |
| 32 | 32 | 547.0 ± 32.3 |

As is apparent from the above results, the hexapeptide compounds were confirmed to promote wound healing of the skins of the rats.

Toxicity Test

An acute toxicity test of peptides Nos. 1, 31 and 32 of the present invention was performed by using, ddY mice. No mice were dead by intravenous injection by 2,000 times (64 μmol/kg) the effective amount. No toxic expression was therefore observed.

Various phermaceutical agent containing the peptide compounds as active ingredients according to the present invention will be described below.

EXAMPLE 35

Peptide No. 1 obtained in Example 1, injection distilled water, sodium chloride, and gelatin were used to obtain an injection in accordance with a conventional injection manufacturing method.

EXAMPLE 36

Peptide No. 2 obtained in Example 2, injection distilled water, sodium chloride, sodium acetate, benzyl alcohol, and gelatin were used to obtain an injection in accordance with the conventional injection manufacturing method.

EXAMPLE 37

Peptide No. 3 obtained in Example 3, injection distilled water, sodium chloride, sodium acetate, gelatin, and phenol were used to obtain an injection in accordance with the conventional injection manufacturing method.

EXAMPLE 38

Peptide No. 4 obtained in Example 4, injection distilled water, sodium chloride, sodium acetate, methyl para-hydroxybenzoate, ethyl para-hydroxybenzoate, propyl para-hydroxybenzoate, and butyl para-hydroxybenzoate were used to obtain an injection in accordance with the conventional injection manufacturing method.

EXAMPLE 39

Peptide No. 5 obtained in Example 5, sodium chloride, sodium acetate, hydrochloric acid, methyl para-hydroxybenzoate, ethyl para-hydroxybenzoate, propyl para-hydroxybenzoate, and butyl para-hydroxybenzoate were used to obtain an injection in accordance with the conventional injection manufacturing method.

EXAMPLE 40

An aqueous solution containing peptide No. 6 obtained in Example 6 and mannitol was freeze-dried. An aqueous solution containing gelatin and phenol was added to the dried product to obtain an injection.

EXAMPLE 41

An aqueous solution containing peptide No. 7 obtained in Example 7, sodium acetate, and human albumin was freeze-dried. Injection distilled water was added to the dried product to obtain an injection.

EXAMPLE 42

Peptide No. 8 obtained in Example 8 and cacao butter or Whitepsole were used to obtain a suppository in accordance with a conventional suppository manufacturing method.

EXAMPLE 43

An aqueous solution containing peptide No. 9 obtained in Example 9, glacial acetic acid, sodium acetate, and benzalkonium chloride was sprayed into a nasal cavity with an intranasal spray applicator to obtain a drug applied to nasal mucous membranes.

EXAMPLE 44

An aqueous solution containing peptide No. 10 obtained in Example 10, glacial acetic acid, sodium acetate, and bile acid salt was sprayed into a nasal cavity with an intranasal spray applicator to obtain a drug applied to nasal mucous membranes.

EXAMPLE 45

Peptide No. 11 obtained in Example 11, and gavakisate methanesulfonate were used to form a capsule in accordance with a conventional capsule manufacturing method.

Additional advantages and modifications will readily occur to those skilled in the art. Therefore, the invention in its broader aspects is not limited to the specific details, representative compounds, and illustrated examples shown and described herein. Accordingly, various modifications may be made without departing from the spirit or scope of the general inventive concept as defined by the appended claims and their equivalents.

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 6 amino acids (B) TYPE: amino acid
(C) STRANDEDNESS: unknown
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=other
/ note="w-guanidinopentanic acid"

(xi) SEQUENCE DESCRIPTION: SEQ ID NO:1:

Xaa Arg Pro Tyr Ile Leu
1               5

(2) INFORMATION FOR SEQ ID NO:4:

(i) SEQUENCE CHARACTERISTICS:
(A) LENGTH: 6 amino acids
(B) TYPE: amino acid
(C) STRANDEDNESS: unknown
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=other
/ note="w-guanidinopentanic acid"

(xi) SEQUENCE DESCRIPTION: SEQ ID NO:4:

Xaa Arg Pro Trp Ile Leu
1               5

(2) INFORMATION FOR SEQ ID NO:6:

(i) SEQUENCE CHARACTERISTICS:
(A) LENGTH: 6 amino acids
(B) TYPE: amino acid
(C) STRANDEDNESS: unknown
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=other
/ note="w-guanidinopentanic acid"

(ix) FEATURE:
(A) NAME/KEY: Modified-site
(B) LOCATION: 6
(D) OTHER INFORMATION: /label=other
/ note="leucine which has one of the hydrogen
atoms of the amino group substituted by a methyl
group"

(xi) SEQUENCE DESCRIPTION: SEQ ID NO:6:

Xaa Arg Pro Tyr Ile Xaa
1               5

(2) INFORMATION FOR SEQ ID NO:9:

(i) SEQUENCE CHARACTERISTICS:
(A) LENGTH: 6 amino acids
(B) TYPE: amino acid
(C) STRANDEDNESS: unknown
(D) TOPOLOGY: linear (ii) MOLECULE TYPE: peptide (ix) FEATURE:
(A) NAME/KEY: Modified-site (B) LOCATION: 1
(D) OTHER INFORMATION: /label=other
/ note="w-guanidinopentanic acid"

(ix) FEATURE:
(A) NAME/KEY: Modified-site
(B) LOCATION: 6
(D) OTHER INFORMATION: /label=other
/ note="leucine which has one of the hydrogen
atoms of the amino group substituted by a methyl
group"

(xi) SEQUENCE DESCRIPTION: SEQ ID NO:9:

Xaa Arg Pro Trp Ile Xaa
1               5

(2) INFORMATION FOR SEQ ID NO:11:

(i) SEQUENCE CHARACTERISTICS:
(A) LENGTH: 6 amino acids
(B) TYPE: amino acid
(C) STRANDEDNESS: unknown
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=other
/ note="w-guanidinopentanic acid"

(ix) FEATURE:
(A) NAME/KEY: Modified-site
(B) LOCATION: 6
(D) OTHER INFORMATION: /label=other
/ note="leucine whose carboxylic group has been
converted into an ethyl ester group"

(xi) SEQUENCE DESCRIPTION: SEQ ID NO:11:

Xaa Arg Pro Tyr Ile Xaa
1               5

(2) INFORMATION FOR SEQ ID NO:14:

(i) SEQUENCE CHARACTERISTICS:
(A) LENGTH: 6 amino acids
(B) TYPE: amino acid
(C) STRANDEDNESS: unknown
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=other
/ note="w-guanidinopentanic acid"

(ix) FEATURE:
(A) NAME/KEY: Modified-site
(B) LOCATION: 6
(D) OTHER INFORMATION: /label=other
/ note="leucine whose carboxylic group has been
converted into an ethyl ester group"

(xi) SEQUENCE DESCRIPTION: SEQ ID NO:14:

Xaa Arg Pro Trp Ile Xaa
1               5

(2) INFORMATION FOR SEQ ID NO:16:

(i) SEQUENCE CHARACTERISTICS:
(A) LENGTH: 6 amino acids
(B) TYPE: amino acid
(C) STRANDEDNESS: unknown ( D ) TOPOLOGY: linear ( i i ) MOLECULE TYPE: peptide ( i x ) FEATURE:
          ( A ) NAME/KEY: Modified-site
          ( B ) LOCATION: 1
          ( D ) OTHER INFORMATION: /label=other
                  / note="w-guanidinopentanic acid"

( i x ) FEATURE:
          ( A ) NAME/KEY: Modified-site
          ( B ) LOCATION: 6
          ( D ) OTHER INFORMATION: /label=other
                  / note="leucine whose carboxylic group has been
                  converted into an ethyl ester group and which has
                  one of the hydrogen atoms of the amino group
                  substituted by a methyl group"

( x i ) SEQUENCE DESCRIPTION: SEQ ID NO:16:

Xaa  Arg  Pro  Tyr  Ile  Xaa
    1                    5

( 2 ) INFORMATION FOR SEQ ID NO:19:

( i ) SEQUENCE CHARACTERISTICS:
          ( A ) LENGTH: 6 amino acids
          ( B ) TYPE: amino acid
          ( C ) STRANDEDNESS: unknown
          ( D ) TOPOLOGY: linear ( i i ) MOLECULE TYPE: peptide ( i x ) FEATURE:
          ( A ) NAME/KEY: Modified-site
          ( B ) LOCATION: 1
          ( D ) OTHER INFORMATION: /label=other
                  / note="w-guanidinopentanic acid"

( i x ) FEATURE:
          ( A ) NAME/KEY: Modified-site
          ( B ) LOCATION: 6
          ( D ) OTHER INFORMATION: /label=other
                  / note="leucine whose carboxylic group has been
                  converted into an ethyl ester group and which has
                  one of the hydrogen atoms of the amino group
                  substituted by a methyl group"

( x i ) SEQUENCE DESCRIPTION: SEQ ID NO:19:

Xaa  Arg  Pro  Trp  Ile  Xaa
    1                    5

( 2 ) INFORMATION FOR SEQ ID NO:21:

( i ) SEQUENCE CHARACTERISTICS:
          ( A ) LENGTH: 6 amino acids
          ( B ) TYPE: amino acid
          ( C ) STRANDEDNESS: unknown
          ( D ) TOPOLOGY: linear ( i i ) MOLECULE TYPE: peptide ( i x ) FEATURE:
          ( A ) NAME/KEY: Modified-site
          ( B ) LOCATION: 1
          ( D ) OTHER INFORMATION: /label=other
                  / note="w-guanidinopentanic acid"

( i x ) FEATURE:
          ( A ) NAME/KEY: Modified-site
          ( B ) LOCATION: 6
          ( D ) OTHER INFORMATION: /label=other
                  / note="leucinol (i.e. - CH2OH group replaces the
                  carboxylic group of leucine"

( x i ) SEQUENCE DESCRIPTION: SEQ ID NO:21:

Xaa  Arg  Pro  Tyr  Ile  Xaa (2) INFORMATION FOR SEQ ID NO:24:

(i) SEQUENCE CHARACTERISTICS:
        (A) LENGTH: 6 amino acids
        (B) TYPE: amino acid
        (C) STRANDEDNESS: unknown
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=other
            /note="w-guanidinopentanic acid"

(ix) FEATURE:
        (A) NAME/KEY: Modified-site
        (B) LOCATION: 6
        (D) OTHER INFORMATION: /label=other
            /note="leucinol (i.e. - CH2OH group replaces the carboxylic group of leucine"

(xi) SEQUENCE DESCRIPTION: SEQ ID NO:24:

Xaa Arg Pro Trp Ile Xaa
    1               5

(2) INFORMATION FOR SEQ ID NO:26:

(i) SEQUENCE CHARACTERISTICS:
        (A) LENGTH: 6 amino acids
        (B) TYPE: amino acid
        (C) STRANDEDNESS: unknown
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=other
            /note="w-guanidinopentanic acid"

(ix) FEATURE:
        (A) NAME/KEY: Modified-site
        (B) LOCATION: 6
        (D) OTHER INFORMATION: /label=other
            /note="leucinol (i.e. - CH2OH group replaces the carboxylic group of leucine) which has one of the hydrogen atoms of the amino group substituted by a methyl group"

(xi) SEQUENCE DESCRIPTION: SEQ ID NO:26:

Xaa Arg Pro Tyr Ile Xaa
    1               5

(2) INFORMATION FOR SEQ ID NO:29:

(i) SEQUENCE CHARACTERISTICS:
        (A) LENGTH: 6 amino acids
        (B) TYPE: amino acid
        (C) STRANDEDNESS: unknown
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=other
            /note="w-guanidinopentanic acid"

(ix) FEATURE:
        (A) NAME/KEY: Modified-site
        (B) LOCATION: 6

-continued (D) OTHER INFORMATION: /label=other
/ note="leucinol (i.e. - CH2OH group replaces the
carboxylic group of leucine), which has one of the
hydrogen atoms of the amino group substituted by a
methyl group"

( x i ) SEQUENCE DESCRIPTION: SEQ ID NO:29:

Xaa Arg Pro Trp Ile Xaa
1               5

( 2 ) INFORMATION FOR SEQ ID NO:31:

( i ) SEQUENCE CHARACTERISTICS:
(A) LENGTH: 6 amino acids
(B) TYPE: amino acid
(C) STRANDEDNESS: unknown
(D) TOPOLOGY: linear ( i i ) MOLECULE TYPE: peptide ( i x ) FEATURE:
(A) NAME/KEY: Modified-site
(B) LOCATION: 1
(D) OTHER INFORMATION: /label=other
/ note="acetylated derivative of arginine"

( i x ) FEATURE:
(A) NAME/KEY: Modified-site
(B) LOCATION: 6
(D) OTHER INFORMATION: /label=other
/ note="leucinol (i.e. - CH2OH group replaces the
carboxylic group of leucine"

( x i ) SEQUENCE DESCRIPTION: SEQ ID NO:31:

Xaa Arg Pro Tyr Ile Xaa
1               5

( 2 ) INFORMATION FOR SEQ ID NO:32:

( i ) SEQUENCE CHARACTERISTICS:
(A) LENGTH: 6 amino acids
(B) TYPE: amino acid
(C) STRANDEDNESS: unknown
(D) TOPOLOGY: linear ( i i ) MOLECULE TYPE: peptide ( i x ) FEATURE:
(A) NAME/KEY: Modified-site
(B) LOCATION: 1
(D) OTHER INFORMATION: /label=other
/ note="acetylated derivative of arginine"

( i x ) FEATURE:
(A) NAME/KEY: Modified-site
(B) LOCATION: 6
(D) OTHER INFORMATION: /label=other
/ note="leucine whose carboxylic group has been
converted into carbamoyl"

( x i ) SEQUENCE DESCRIPTION: SEQ ID NO:32:

Xaa Arg Pro Tyr Ile Xaa
1               5

( 2 ) INFORMATION FOR SEQ ID NO:33:

( i ) SEQUENCE CHARACTERISTICS:
(A) LENGTH: 6 amino acids
(B) TYPE: amino acid
(C) STRANDEDNESS: unknown
(D) TOPOLOGY: linear ( i i ) MOLECULE TYPE: peptide ( i x ) FEATURE:
(A) NAME/KEY: Modified-site

```
       (B) LOCATION: 1
       (D) OTHER INFORMATION: /label=other
            / note="butylated derivative of arginine"

(ix) FEATURE:
       (A) NAME/KEY: Modified-site
       (B) LOCATION: 6
       (D) OTHER INFORMATION: /label=other
            / note="leucinol (i.e. - CH2OH group replaces the
              carboxylic group of leucine"

(xi) SEQUENCE DESCRIPTION: SEQ ID NO:33:

Xaa  Arg  Pro  Tyr  Ile  Xaa
  1                        5

(2) INFORMATION FOR SEQ ID NO:34:

(i) SEQUENCE CHARACTERISTICS:
       (A) LENGTH: 6 amino acids
       (B) TYPE: amino acid
       (C) STRANDEDNESS: unknown
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /label=other
            / note="butylated derivative of arginine"

(ix) FEATURE:
       (A) NAME/KEY: Modified-site
       (B) LOCATION: 6
       (D) OTHER INFORMATION: /label=other
            / note="leucine whose carboxylic group has been
              converted into carbamoyl"

(xi) SEQUENCE DESCRIPTION: SEQ ID NO:34:

Xaa  Arg  Pro  Tyr  Ile  Xaa
  1                        5
```

What is claimed is:

1. A hexapeptide of the formula (I):

A-B-Pro-C-D-E     (I)

where A is an L- or D- form of arginine or lysine, the N-terminal amino group of which is deaminated, B is an L- or D- form of arginine, lysine, or histidine, Pro is an L- or D- form of proline, C is an L- or D- form of tyrosine, tryptophan, or phenylalanine, D is an L- or D- form of valine, isoleucine, or leucine, and E is an L- or D- form of valine, isoleucine, or leucine, one of the hydrogen atoms of the amino group of which may be substituted with a $C_1$ to $C_4$ alkyl group, and the C-terminal carboxyl group of which is substituted with —CH$_2$OR, wherein R is a hydrogen atom or a $C_1$ to $C_4$ alkyl group;

or a pharmaceutically acceptable salt of the hexapeptide.

2. A hexapeptide of the formula (II):

A-B-Pro-C-D-E     (II)

where A is an L- or D- form of arginine or lysine, the N-terminal amino group of which is alkylated or acylated, B is an L- or D- form of arginine, lysine, or histidine, Pro is an L- or D- form of proline, C is an L- or D- form of tyrosine, tryptophan, or phenylalanine, D is an L- or D- form of valine, isoleucine, or leucine and E is an L- or D- form of valine, isoleucine, or leucine, one of the hydrogen atoms of the amino group of which is substituted with a $C_1$ to $C_4$ alkyl group, and the C-terminal carboxyl group of which is substituted with —CH$_2$OR, wherein R is a hydrogen atom or a $C_1$ to $C_4$ alkyl group;

or a pharmaceutically acceptable salt of the hexapeptide.

3. A pharmaceutical agent comprising, as an active ingredient, a hexapeptide of the formula (I):

A-B-Pro-C-D-E     (I)

where A is an L- or D- form of arginine or lysine the N-terminal amino group of which is deaminated, B is an L- or D- form of arginine, lysine, or histidine, Pro is an L- or D- form of proline, C is an L- or D- form of tyrosine, tryptophan, or phenylalanine, D is an L- or D- form of valine, isoleucine, or leucine, and E is an L- or D- form of valine, isoleucine, or leucine, one of the hydrogen atoms of the amino group of which may be substituted with a $C_1$ to $C_4$ alkyl group, and the C-terminal carboxyl group of which is substituted with —CH$_2$OR , wherein R is a hydrogen atom or a $C_1$ to $C_4$ alkyl group, or a pharmaceutically acceptable salt of the hexapeptide; and a pharmaceutically acceptable carrier.

4. The pharmaceutical agent according to claim 3, wherein said agent is selected from the group consisting of an anti-allergic agent, a wound healing agent, and an anti-inflammatory agent.

5. A pharmaceutical agent comprising, as an active ingredient, a hexapeptide of the formula (II):

A-B-Pro-C-D-E     (II)

where A is an L- or D- form of arginine or lysine the N-terminal amino group of which is alkylated or acylated, B is an L- or D- form of arginine, lysine, or histidine, Pro is an L- or D- form of proline, C is an L- or D- form of tyrosine, tryptophan, or phenylalanine, D is an L- or D- form of valine, isoleucine, or leucine, and E is an L- or D- form of valine, isoleucine, or leucine, one of the hydrogen atoms of the amino group of which is substituted with a $C_1$ to $C_4$ alkyl group, and the C-terminal carboxyl group of which is substituted with —$CH_2OR$, wherein R is a hydrogen atom or a $C_1$ to $C_4$ alkyl group, or a pharmaceutically acceptable salt of the hexapeptide; and a pharmaceutically acceptable carrier.

6. The pharmaceutical agent according to claim 5, wherein said agent is selected from the group consisting of an anti-allergic agent, a wound healing agent, and an anti-inflammatory agent.

* * * * *